US010806966B2

(12) United States Patent
Shim et al.

(10) Patent No.: US 10,806,966 B2
(45) Date of Patent: Oct. 20, 2020

(54) MOTION ASSISTANCE APPARATUS

(71) Applicant: Samsung Electronics Co., Ltd., Suwon-si, Gyeonggi-do (KR)

(72) Inventors: Youngbo Shim, Seoul (KR); Jongwon Lee, Suwon-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 639 days.

(21) Appl. No.: 15/609,763

(22) Filed: May 31, 2017

(65) Prior Publication Data

US 2018/0177670 A1    Jun. 28, 2018

(30) Foreign Application Priority Data

Dec. 28, 2016   (KR) ........................ 10-2016-0181137

(51) Int. Cl.
*A63B 23/04* (2006.01)
*A63B 21/00* (2006.01)
(Continued)

(52) U.S. Cl.
CPC ........ *A63B 23/0494* (2013.01); *A61F 5/0102* (2013.01); *A61H 1/0237* (2013.01); *A61H 1/0262* (2013.01); *A61H 3/00* (2013.01); *A63B 21/00181* (2013.01); *A63B 21/068* (2013.01); *A63B 23/0482* (2013.01); *B25J 9/0006* (2013.01); *A61F 2005/0155* (2013.01); *A61F 2005/0158* (2013.01);
(Continued)

(58) Field of Classification Search
CPC ......................... A63B 23/0494; A61H 1/0237; A61H 1/0262; A61H 3/00; A61H 3/008; A61H 2003/001; B25J 9/0006; B25J 17/0258; F16F 1/128
See application file for complete search history.

(56) References Cited

U.S. PATENT DOCUMENTS 8,079,967 B2    12/2011  Ikeuchi et al.
8,093,475 B1 *   1/2012  Sperzel ................... G10D 3/14
                                              84/312 R
(Continued)

FOREIGN PATENT DOCUMENTS

JP              5799519 B2      10/2015
KR      10-2015-0139056 A       12/2015
(Continued)

OTHER PUBLICATIONS

"Effects of the Lower Leg Bi-Articular Muscle in Jumping", Journal of Robotics and Mechatronics, Journal of Robotics and Mechatronics vol. 16 Nov. 6, 2004.

*Primary Examiner* — Timothy A Stanis
*Assistant Examiner* — Charles M Vivian
(74) *Attorney, Agent, or Firm* — Harness, Dickey & Pierce, P.L.C.

(57) ABSTRACT

A motion assistance apparatus including a first frame, a connection frame connected to the first frame, the connection frame configured to rotate relative to the first frame, a second frame connected to the connection frame, the second frame configured to rotate relative to the connection frame, and a power transmission member configured to change, based on a first angle between the first frame and the connection frame, a second angle between the connection frame and the second frame.

15 Claims, 10 Drawing Sheets

(51) Int. Cl.
*A63B 21/068* (2006.01)
*A63B 23/02* (2006.01)
*B25J 9/00* (2006.01)
*A61F 5/01* (2006.01)
*A61H 3/00* (2006.01)
*A61H 1/02* (2006.01)

(52) U.S. Cl.
CPC ......... *A61F 2005/0188* (2013.01); *A61H 2201/0192* (2013.01); *A61H 2201/163* (2013.01); *A61H 2201/165* (2013.01); *A61H 2201/1642* (2013.01); *A61H 2201/1652* (2013.01); *A61H 2201/503* (2013.01); *A61H 2201/5053* (2013.01); *A63B 21/154* (2013.01); *A63B 21/4009* (2015.10); *A63B 21/4011* (2015.10); *A63B 21/4025* (2015.10); *A63B 21/4033* (2015.10); *A63B 21/4047* (2015.10); *A63B 23/0211* (2013.01); *A63B 2023/0411* (2013.01); *A63B 2220/24* (2013.01); *A63B 2220/803* (2013.01)

(56) References Cited

U.S. PATENT DOCUMENTS

| | | |
|---|---|---|
| 8,114,034 B2 | 2/2012 | Ikeuchi et al. |
| 8,177,733 B2 | 5/2012 | Ashihara et al. |
| 8,986,233 B2 | 3/2015 | Aoki et al. |
| 9,168,195 B2 | 10/2015 | Sankai |
| 9,216,131 B2 | 12/2015 | Nakashima et al. |
| 9,351,900 B2 | 5/2016 | Walsh et al. |
| 2003/0178758 A1* | 9/2003 | Metelski ............... F16F 1/06 267/166 |
| 2013/0296746 A1 | 11/2013 | Herr et al. |
| 2014/0100492 A1 | 4/2014 | Nagasaka |
| 2015/0016923 A1* | 1/2015 | Brown ................ A61F 5/01 414/1 |
| 2015/0321342 A1* | 11/2015 | Smith ............... B25J 9/0009 74/490.03 |
| 2016/0199685 A1* | 7/2016 | von Hoffmann .. A63B 21/4025 482/8 |
| 2016/0229055 A1 | 8/2016 | Kim et al. |
| 2018/0177672 A1* | 6/2018 | Uchida ................ A61H 3/00 |
| 2019/0015286 A1* | 1/2019 | Glaister ............... A61F 5/01 |

FOREIGN PATENT DOCUMENTS

| | | |
|---|---|---|
| KR | 10-2016-0067819 A | 6/2016 |
| WO | WO-2009/040987 A1 | 4/2009 |
| WO | WO-2009/050839 A1 | 4/2009 |
| WO | WO-2010/052824 A1 | 5/2010 |
| WO | WO-2016/089466 A2 | 9/2016 |

* cited by examiner

MOTION ASSISTANCE APPARATUS

CROSS-REFERENCE TO RELATED APPLICATION

This application claims priority under 35 U.S.C. § 119 to Korean Patent Application No. 10-2016-0181137, filed on Dec. 28, 2016, in the Korean Intellectual Property Office, the entire contents of which are incorporated herein by reference.

BACKGROUND

1. Field

Some example embodiments relate to motion assistance apparatuses.

2. Description of the Related Art

With the onset of the aging society, many persons experience joint pain and/or joint inconveniences. Interest in motion assistance apparatuses that enable the elderly and/or patients having joint problems to walk with less effort is on the increase. Further, motion assistance apparatuses increasing muscular strength of users for military purposes are being developed.

SUMMARY

Some example embodiments relate to motion assistance apparatuses.

In some example embodiments, the motion assistance apparatus may include a first frame, a connection frame connected to the first frame, the connection frame configured to rotate relative to the first frame, a second frame connected to the second frame, the second frame configured to rotate relative to the connection frame, and a power transmission member configured to change, based on a first angle between the first frame and the connection frame, a second angle between the connection frame and the second frame.

The motion assistance apparatus may further include a first joint configured to connect the first frame and the connection frame, and a second joint configured to connect the connection frame and the second frame.

The power transmission member may be configured to wind around the first joint and the second joint.

The first joint may include a first idler configured to rotate on an outer-surface of the first joint, and at least a portion of the power transmission member is configured to wind around the first idler, and the second joint may include a second idler configured to rotate on an outer surface of the second joint, and at least a portion of the power transmission member is configured to wind around the first idler the second idler.

In response to the connection frame rotating in a direction in which the first angle increases relative to the first frame, a length of the power transmission member wound around the first joint may increase, a length of the power transmission member wound around the second joint may decrease, and the second angle may increase.

The motion assistance apparatus may further include a first guide on the first frame, the first guide adjacent to the first joint, and the first guide configured to guide the power transmission member to be in contact with a portion of an outer circumference of the first joint, a second guide on the connection frame, the second guide adjacent to the first joint, and the second guide configured to guide the power transmission member to be in contact with another portion of the outer circumference of the first joint, a third guide on the connection frame, the third guide adjacent to the second joint, and the third guide configured to guide the power transmission member to be in contact with a portion of an outer circumference of the second joint, and a fourth guide provided to the second frame to be adjacent to the second joint, and configured to guide the power transmission member to be in contact with another portion of the outer circumference of the second joint.

The power transmission member may be configured to wind around the first guide, the first joint, the second guide, the third guide, the second joint, and the fourth guide sequentially.

At least one of the first guide, the second guide, the third guide, and the fourth guide may be configured to rotate.

Both ends of the power transmission member may be fixed to the first frame and the second frame, respectively.

At least one of the first frame and the second frame may further include a length adjusting device configured to adjust a length of the power transmission member, and one end of the power transmission member may be fixed to the length adjusting device.

The length adjusting device may include a pinion gear to which one end of the power transmission member is fixed, and a worm gear configured to engage into the pinion gear.

The power transmission member may have elasticity.

The power transmission member may include a first cable configured to connect to the first frame, a second cable configured to connect to the second frame, and a slack adjusting device configured to connect to both the first cable and the second cable.

The slack adjusting device may include a base configured to connect to one of the first cable and the second cable, a slider configured to connect to another one of the first cable and the second cable, the slider configured to slide along the base, and an elastic body between the slider and the base.

The slack adjusting device may further include a buffering member configured to buffer an impact of the slider against the base.

The connection frame may include an engager configured to restrict an angle between the connection frame and the second frame to be a threshold angle or less.

The first frame may include a first support configured to support a first part of the user, the connection frame may include a connection support configured to support a second part of the user, the second part connected to the first part through a single joint, and the second frame may include a second support configured to support a third part of the user, the third part connected to the second part through a single joint.

In some example embodiments, the motion assistance apparatus may include a first frame configured to support a first part of a user, a connection frame configured to support a second part of the user, the connection frame connected to the first frame, the connection frame configured to rotate relative to the first frame, a first joint configured to connect the first frame and the connection frame, a second frame configured to support a third part of the user, the second frame connected to the connection frame, the second frame configured to rotate relative to the connection frame, a second joint configured to connect the connection frame and the second frame, a third frame configured to support a fourth part of the user, and a power transmission member including a first end, a second end, and a middle area between the first end and the second end, the first end fixed to the first frame, the second end fixed to the third frame, the middle area winding around the first joint and the second joint.

The power transmission member may be configured to change an angle between the second frame and the third frame based on a length of the power transmission member being wound around each of the first joint and the second joint.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of some example embodiments, taken in conjunction with the accompanying drawings of which.

DETAILED DESCRIPTION

Figure 1:
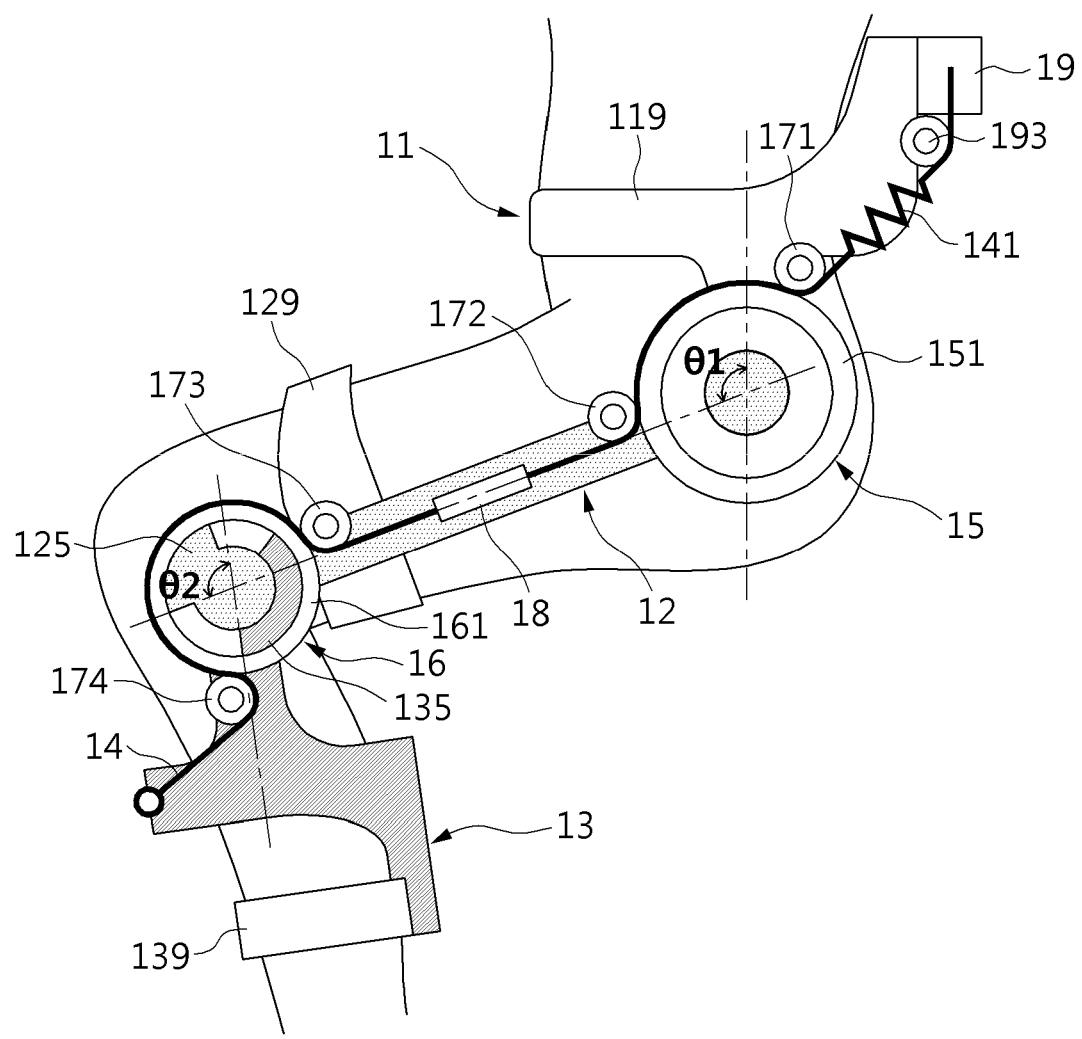
FIG. 1 is a side view of a motion assistance apparatus according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of the example embodiments described herein, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives falling within the scope of the inventive concepts. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Various example embodiments will now be described more fully with reference to the accompanying drawings in which some example embodiments are shown. In the drawings, the thicknesses of layers and regions are exaggerated for clarity.

Figure 2:
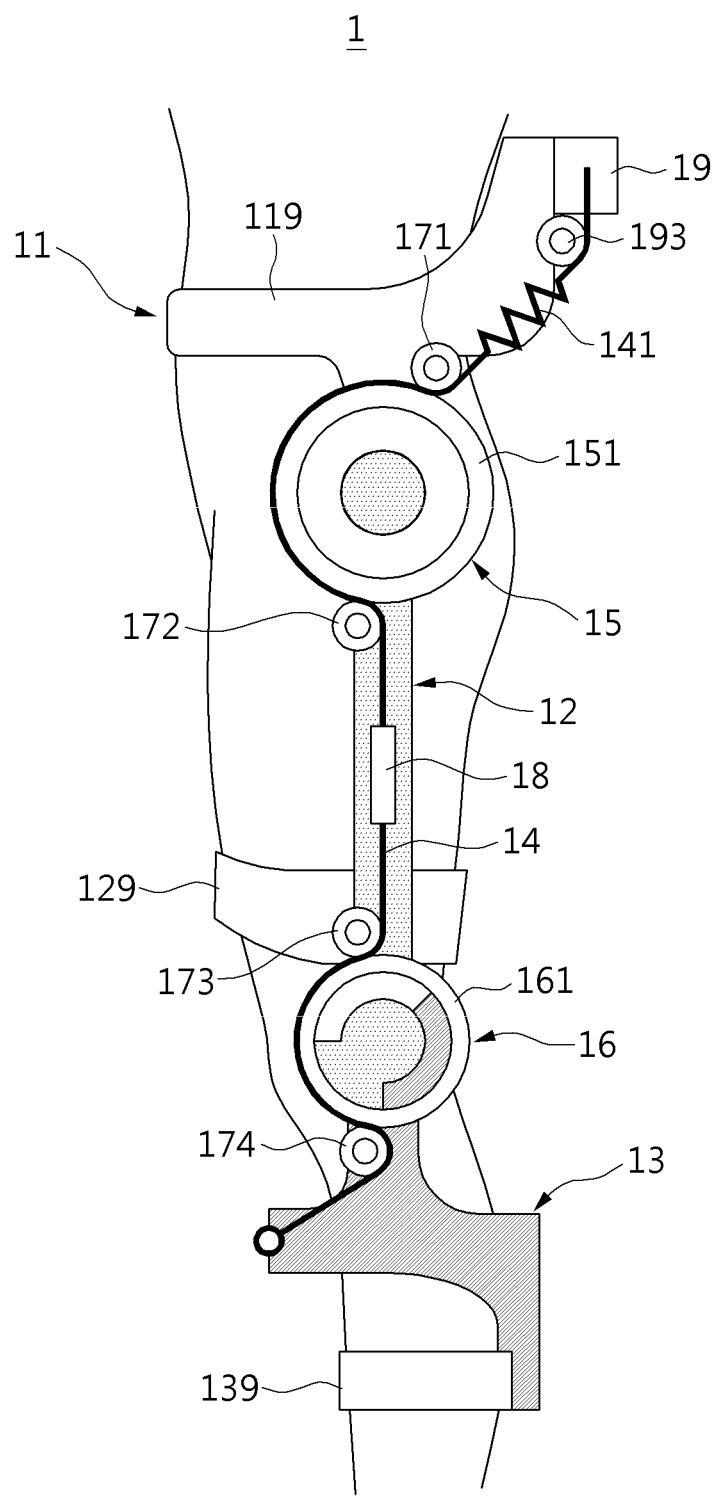
FIG. 2 is a side view of a motion assistance apparatus according to at least one example embodiment.

FIGS. 1 and 2 are side views of a motion assistance apparatus according to at least one example embodiment. In detail, FIG. 1 illustrates an example in which a hip joint and a knee joint of a user wearing a motion assistance apparatus according to the at least one example embodiment are in a flexion state. FIG. 2 illustrates an example in which the hip joint and the knee joint of the user wearing the motion assistance apparatus are in an extension state.

Referring to FIGS. 1 and 2, a motion assistance apparatus 1 may assist a motion between adjacent two joints of a user, for example, a hip joint motion and a knee joint motion. The motion assistance apparatus 1 may assist the user with flexion and extension of the hip joint of the user, for example, when the user is walking on the flatland. The motion assistance apparatus 1 may assist the user with interaction between the hip joint and the knee joint of the user when the user is doing an exercise (e.g., a step-up motion, a slope walking motion, or a sitting-and-standing motion) of giving a burden to the knee joint rather than a general flat gait.

The motion assistance apparatus 1 may be supplied with power from an actuator disposed on a portion of a body of the user or the motion assistance apparatus 1. For example, the motion assistance apparatus 1 may include a sensor configured to sense a movement of the user, and the actuator may receive a signal from the sensor and may supply the power suitable for a gait stage of the user.

The motion assistance apparatus 1 may include a first frame 11, a connection frame 12, a second frame 13, a power transmission member 14, a first joint 15, a second joint 16, guides 171, 172, 173, and 174, a slack adjusting device 18, and a length adjusting device 19.

The motion assistance apparatus 1 may assist an extension motion or a flexion motion of the hip joint of the user through the actuator. For example, when the hip joint of the user is to be extended, the actuator may transfer the power to the connection frame 12 such that a first angle $\theta 1$ between the connection frame 12 and the first frame 11 increases. In this case, an interaction between the hip joint and the knee joint may assist the knee joint in an extension direction. That is, in response to an extension of the hip joint of the user, a length of the power transmission member 14 that is wound around the first joint 15 may increase and the power transmission member 14 may push the second frame 13 up in a direction in which the knee joint extends in order to secure the winding length. Through this mechanism, the motion assistance apparatus 1 may assist the user having restricted knee strength with performing a step-up motion, a slope-walking motion, a sitting-and-standing motion, and the like.

When the hip joint of the user is to be flexed, for example, when the user is performing a squat motion, the actuator may transfer the power to the connection frame 12 such that the first angle θ1 between the connection frame 12 and the first frame 11 decreases. In this case, an interaction between the hip joint and the knee joint may prevent an excessive flexion of the knee joint. That is, in response to a flexion of the hip joint of the user, a length of the power transmission member 14 that is wound around the first joint 15 may decrease and the power transmission member 14 may be further wound around the second joint 16 by a reduced length. In this case, the power transmission member 14 may prevent a flexion of the knee joint of the user beyond the additionally winding length. Through this mechanism, when the user having restricted knee strength is performing a squat motion, the motion assistance apparatus 1 may prevent the user from falling back by restricting an excessive flexion of the knee joint.

The first frame 11 may support a first part of the user. The first frame 11 may include a first support 119 configured to support the first part of the user. For example, the first support 119 may support the waist and/or pelvis of the user. A circumferential size of the first support 119 may be adjusted to fit a circumferential size of the waist and/or pelvis of the user to improve the fit the user feels and to prevent a shaking from occurring. Further, because the first support makes a close contact with the body of the user, the user may wear clothes over the motion assistance apparatus 1.

The connection frame 12 may be connected to be rotatable relative to the first frame 11. For example, the connection frame 12 may be hinge-connected to the first frame 11.

The connection frame 12 may support a second part of the user connected to the first part of the user through a single joint. For example, the connection frame 12 may support a thigh that is connected to the waist and/or pelvis of the user through the hip joint. For example, the connection frame 12 may include the length adjusting device 19 which adjusts a length based on a length between the hip joint and the knee joint of the user. The connection frame 12 may include a connection support 129 configured to support the second part.

The connection support 129 may surround the second part of the user such that that the thigh of the user may move along a movement of the connection frame 12. For example, the connection support 129 may be in close contact with a thigh portion of the user. A circumferential size of the connection support 129 may be adjusted to fit a circumferential size of the thigh of the user.

The first joint 15 may connect the first frame 11 and the connection frame 12. For example, a first part that is extended from the first frame 11 and a second part that is extended from the connection frame 12 may be hinge-connected to each other. In this case, the first part and the second part may be referred to as the first joint 15.

The first frame 11 and the connection frame 12 may be relatively rotatable based on the first joint 15. The first angle θ1 between first frame 11 and the connection frame 12 may vary in response to a flexion and an extension of the hip joint of the user. The first angle θ1 may be provided to correspond to an angle with the hip joint of the user. The first joint 15 may be disposed in parallel with the hip joint to have the same rotating shaft as a rotating shaft associated with the flexion and the extension of the hip joint of the user.

A portion of the power transmission member 14 may be wound around the first joint 15. A winding length of the power transmission member 14 may vary based on the first angle θ1 between the first frame 11 and the connection frame 12. For example, when the power transmission member 14 is wound around the first joint 15 on a front side of the user as shown in FIG. 1, a length of the power transmission member 14 that is wound around the first joint 15 may increase according to an increase in the first angle θ1. The first joint 15 may include a first idler 151.

The first idler 151 may be provided to be idle-rotatable on the outer side of the first joint 15. The first idler 151 is positioned on the same shaft of the first joint 15 and may independently rotate without being constrained by the first frame 11 and the connection frame 12. In response to an increase or a decrease in the first angle θ1, the first idler 151 may rotate on the outer surface of the first joint 15. In response to the rotation of the first idler 151, the length of the power transmission member 14 that is wound around the first idler 151 may increase or decrease. The first idler 151 may prevent a direct friction between the power transmission member 14 and the first joint 15, and may reduce damage and heat generation of the power transmission member 14.

The second frame 13 may be connected to be rotatable relative to the connection frame 12. For example, the second frame 13 may be hinge-connected to the connection frame 12. The second frame 13 may support a third part that is connected to the second part of the user using a single joint. For example, the second frame 13 may support a shank and/or a calf of the user that is connected to a thigh of the user through the knee joint of the user. The second frame 13 may include a second support 139 configured to support the third part of the user.

The second support 139 may surround the third part of the user so that the shank and/or the calf of the user may move according to a movement of the second frame 13. For example, the second support 139 may be in close contact with the shank and/or the calf of the user. Here, the second support 139 may include a detachable belt of which a circumferential size is adjusted to fit a circumferential size of the shank and/or the calf of the user.

The second joint 16 may connect the connection frame 12 and the second frame 13. For example, a third part that is extended from the connection frame 12 and a fourth part that is extended from the second frame 13 may be hinge-connected. In this case, the third part and the fourth part may be referred to as the second joint 16.

The connection frame 12 and the second frame 13 may be relatively rotatable based on the second joint 16. A second angle θ2 between the connection frame 12 and the second frame 13 may vary based on a flexion and an extension of the knee joint of the user. The second angle θ2 may be provided to correspond to an angle with the knee joint of the user and the second joint 16 may be disposed in parallel with the knee joint to have the same shaft as that of the knee joint of the user.

A portion of the power transmission member 14 may be wound around the second joint 16. A winding length of the power transmission member 14 may vary based on the second angle θ2 between the connection frame 12 and the second frame 13. For example, when the power transmission member 14 is wound around the second joint 16 on the front side of the user as shown in FIG. 1, a length of the power transmission member 14 that is wound around the second joint 16 may increase according to an increase in the second angle θ2. The second joint 16 may include a second idler 161.

The second idler 161 may be provided to be idle-rotatable on the outer side of the second joint 16. The second idler 161 may be disposed on the same shaft of the second joint 16 and may independently rotate without being constrained by the connection frame 12 and the second frame 13. In response to an increase or a decrease in the second angle θ2, the second idler 161 may rotate on the outer side of the second joint 16. In response to rotation of the second idler 161, the length of the power transmission member 14 that is wound around the second idler 161 may increase or decrease. The second idler 161 may prevent a direct friction between the power transmission member 14 and the second joint 16, and may reduce damage and heat generation of the power transmission member 14.

A portion of the power transmission member 14 may be wound around the first joint 15 and the second joint 16. Both ends of the power transmission member 14 may be fixed to the first frame 11 and the second frame 13, respectively. According to the above structure, a total length of the power transmission member 14 in the motion assistance apparatus 1 may be determined as a desired (or alternatively, predetermined) length. Thus, in response to an increase in a length of the power transmission member 14 that is wound around the first joint 15, a length of the power transmission member 14 that is wound around the second joint 16 may decrease to secure a length of the power transmission member 14 to be wound around the first joint 15.

The power transmission member 14 may change the second angle θ2 between the connection frame 12 and the second frame 13 based on the first angle θ1 between the first frame 11 and the connection frame 12. Hereinafter, a process in which the first angle θ1 and the second angle θ2 interactively change by way of the power transmission member 14 will be described.

The actuator provided to a portion of the body of the user or the motion assistance apparatus 1 may detect a motion of the user and may transfer the power to the connection frame 12 so that the first angle θ1 may increase in response to the hip joint of the user that is to be extended. In this case, the length of the power transmission member 14 that is wound around the first joint 15 may increase. According to an increase in the length of the power transmission member 14 that is wound around the first joint 15, a tension of the power transmission member 14 may increase. The increased tension of the power transmission member 14 may act as an auxiliary power to increase the second angle θ2. That is, a single actuator configured to transfer the power to the connection frame 12 may simultaneously assist the extension of the hip joint and the knee joint of the user by simultaneously changing the first angle θ1 and the second angle θ2.

The actuator provided to a portion of the body of the user or the motion assistance apparatus 1 may detect a motion of the user, and may transfer the power to the connection frame 12 so that the first angle θ1 may decrease in response to the hip joint of the user that is to be flexed or bent. In this case, the length of the power transmission member 14 that is wound around the first joint 15 may decrease. According to a decrease in the length of the power transmission member 14 that is wound around the first joint 15, a length of the power transmission member 14 that is wound around the second joint 16 may increase and the second angle θ2 may decrease. A variation in the length of the power transmission member 14 that is wound around the second joint 16 may be restricted to be less than or equal to a variation in the length of the power transmission member 14 that is wound around the first joint 15. That is, the power transmission member 14 may provide a counter force to the connection frame 12 and the second frame 13 to prevent a knee joint flexion angle from increasing compared to a hip joint flexion angle. According to the above structure, the power transmission member 14 may restrict the knee joint of the user not to be excessively flexed against the hip joint during a flexion of the hip joint of the user.

The power transmission member 14 may include, for example, a spring configured to linearly change the tension of the power transmission member 14. As another example, the power transmission member 14 may be an elastic material to not cause a burden to the user due to a sudden occurrence of the tension. For example, the power transmission member 14 may be a material, such as rubber, and the like.

The guides 171, 172, 173, and 174 may guide the power transmission member 14 so that the power transmission member 14 may be wound around the first joint 15 and the second joint 16 without being separated from the first joint 15 and the second joint 16. The guides 171, 172, 173, and 174 may also be referred to as a first guide 171, a second guide 172, a third guide 173, and a fourth guide 174.

The first guide 171 may be provided to the first frame 11 to be adjacent to the first joint 15, and may guide the power transmission member 14 to make a contact with a portion of the outer circumference of the first joint 15. For example, the first guide 171 may be rotatably mounted to the first frame 11.

The second guide 172 may be provided to the connection frame 12 to be adjacent to the first joint 15, and may guide the power transmission member 14 to make a contact with a portion of the outer circumference of the first joint 15. For example, the second guide 172 may be rotatably mounted to the connection frame 12.

The first guide 171 and the second guide 172 may determine a contact boundary between the power transmission member 14 and the first joint 15. That is, the first guide 171 and the second guide 172 may guide the power transmission member 14 to be wound around the circumferential curved surface of the first joint 15 from between the first guide 171 and the first joint 15 to between the second guide 172 and the first joint 15. A distance between the first guide 171 and the second guide 172 may vary based on a size of the first angle θ1 along the circumferential curved surface of the first joint 15. Due to this structure, the length of the power transmission member 14 that is wound around the first joint 15 may linearly increase or decrease based on a change in the size of the first angle θ1.

The third guide 173 may be provided to the connection frame 12 to be adjacent to the second joint 16, and may guide the power transmission member 14 to make a contact with a portion of the outer circumference of the second joint 16. Also, the third guide 173 may be rotatably mounted to the connection frame 12.

The fourth guide 174 may be provided to the second frame 13 to be adjacent to the second joint 16, and may guide the power transmission member 14 to make a contact with a portion of the outer circumference of the second joint 16. Also, the fourth guide 174 may be rotatably mounted to the second frame 13.

The third guide 173 and the fourth guide 174 may determine a contact boundary between the power transmission member 14 and the second joint 16. That is, the third guide 173 and the fourth guide 174 may guide the power transmission member 14 to be wound around the circumferential curved surface of the second joint 16 from between the third guide 173 and the second joint 16 to between the fourth guide 174 and the second joint 16. A distance between the third guide 173 and the fourth guide 174 may vary based on a change in a size of the second angle θ2 along the circumferential curved surface of the second joint 16. Due to this structure, the length of the power transmission member 14 that is wound around the second joint 16 may linearly increase or decrease based on the change in the size of the second angle θ2.

The power transmission member 14 may be sequentially wound around the first guide 171, the first joint 15, the second guide 172, the third guide 173, the second joint 16, and the fourth guide 174. At least one of the guides 171, 172, 173, and 174 may be rotatably provided. Due to the rotatably provided guides 171, 172, 173, and/or 174, a length of the power transmission member 14 that are wound around the first joint 15 and the second joint 16 may adaptively vary. Further, damage and heat generation of the power transmission member 14 by friction may decrease.

The slack adjusting device 18 may prevent the power transmission member 14 from being slack (e.g., being loosened or being dropped) in the middle. The slack adjusting device 18 may be provided on a way of the power transmission member 14.

The length adjusting device 19 may adjust the length of the power transmission member 14. The length adjusting device 19 may be provided to at least one of the first frame 11 and the second frame 13. The user may adjust the length of the power transmission member 14 to fit a body size of the user through the length adjusting device 19. Hereinafter, an example in which the length adjusting device 19 is provided to the first frame 11 will be described. In this example, one end of the power transmission member 14 may be fixed to the length adjusting device 19 and another end of the power transmission member 14 may be fixed to the second frame 13.

Figure 3:
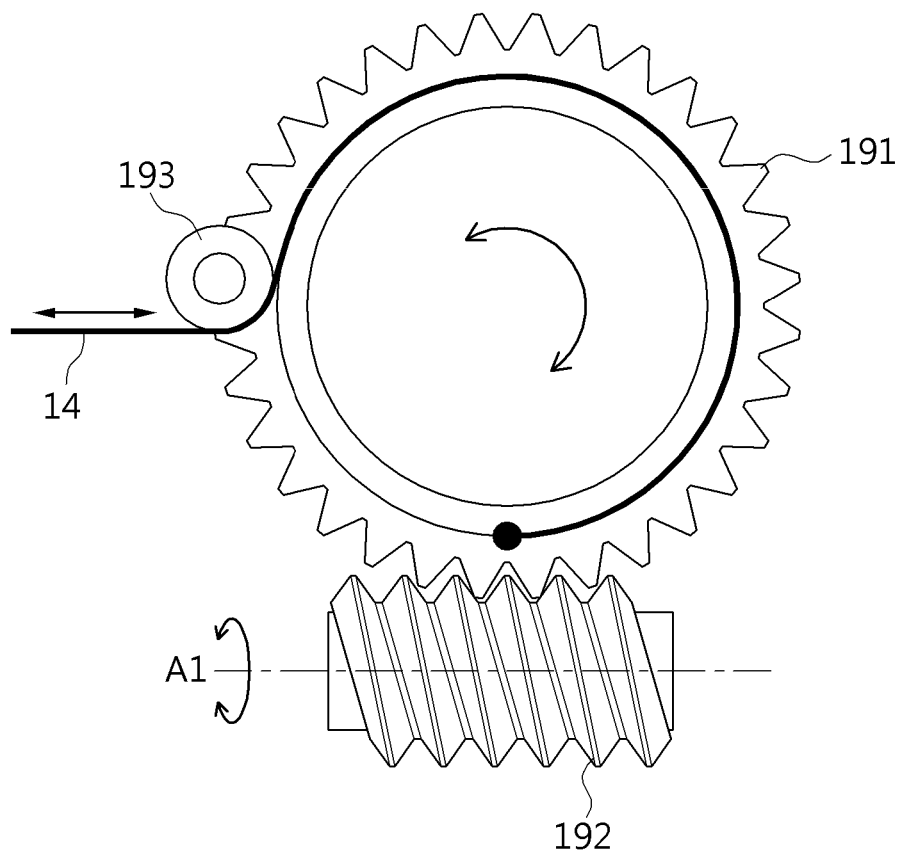
FIG. 3 illustrates an inside of a length adjusting device according to at least one example embodiment.

FIG. 3 illustrates an inside of a length adjusting device according to at least one example embodiment.

Referring to FIG. 3, the length adjusting device 19 refers to a device that adjusts a length of the power transmission member 14 from the length adjusting device 19 to the second frame 13. The length of the power transmission member 14 may be adjusted based on a lower body size of the user through the length adjusting device 19. The length adjusting device 19 may include a pinion gear 191 to which one end of the power transmission member 14 is fixed, a worm gear 192 configured to engage into the pinion gear 191, and an adjusting guide 193.

In response to the user rotating the worm gear 192 in one direction based on a rotating shaft A1, the pinion gear 191 may rotate counterclockwise, a length of the power transmission member 14 that is wound around the pinion gear 191 may decrease, and the length of the power transmission member 14 from the length adjusting device 19 to the second frame 13 may increase. In response to the user rotating the worm gear 192 in an opposite direction to the one direction, the pinion gear 191 may rotate clockwise, the length of the power transmission member 14 that is wound around the pinion gear 191 may increase, and the length of the power transmission member 14 from the length adjusting device 19 to the second frame 13 may decrease.

The worm gear 192 may decrease back-drivability of the length adjusting device 19. The user may change a desired or set length of the power transmission member 14 by rotating the worm gear 192.

The adjusting guide 193 may guide the power transmission member 14 to be wound around the pinion gear 191 without being separated from the pinion gear 191. Due to the adjusting guide 193, the length of the power transmission member 14 that is wound around the pinion gear 191 may linearly increase or decrease based on a rotational angle of the pinion gear 191.

Figure 4:
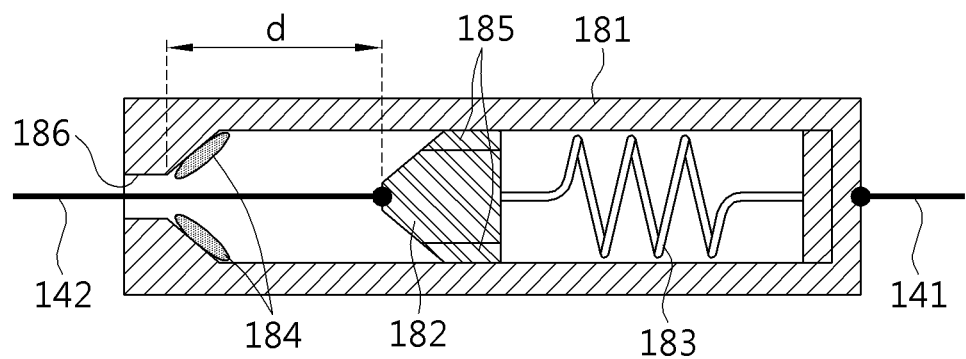
FIG. 4 is a cross-sectional view of a slack adjusting device according to at least one example embodiment.

FIG. 4 is a cross-sectional view of a slack adjusting device according to at least one example embodiment.

Referring to FIG. 4, the slack adjusting device 18 may be provided on a way of the power transmission member 14 and may prevent a slack of the power transmission member 14. The slack adjusting device 18 may include a base 181, a slider 182, an elastic body 183, a buffering member 184, and a bush 185. The power transmission member 14 may include a first cable 141 connected to the first frame 11 and a second cable 142 connected to the second frame 13. The first cable 141 and the second cable 142 may extend from the slack adjusting device 18 in opposite directions, respectively. One of the first cable 141 and the second cable 142 may be connected to the base 181 and the other one of the first cable 141 and the second cable 142 may be connected to the slider 182. Hereinafter, an example in which the first cable 141 is connected to the base 181 and the second cable 142 is connected to the slider 182 will be described.

The base 181 may include an accommodation space inside the base 181, and the slider 182, the elastic body 183, the buffering member 184, and the bush 185 may be disposed in the accommodation space. The base 181 may include a hole 186 through which the second cable 142 passes.

The slider 182 may slide within the accommodation space of the base 181, and a distance d between the hole 186 and the slider 182 may vary based on a movement of the slider 182.

The elastic body 183 may be disposed between the base 181 and the slider 182. The elasticity of the elastic body 183 may be less than that of the power transmission member 14. If the distance d between the hole 186 and the slider 182 is greater than a desired or minimum distance, the slider 182 may be separate from the hole 186 and may slide within the base 181. In this case, although the hip joint is in a fixed state, the user may bend or extend the knee of the user. For example, if the user is to bend the knee, the length of the power transmission member 14 that is wound around the second joint 16 may increase and the power transmission member 14 may pull the slider 182 toward the hole 186. Because the knee of the user only needs to resist the elasticity of the elastic body 183, the degree of freedom of the knee joint may be generated.

The slack adjusting device 18 configured as above may be applied to give a clearance angle to a flexion direction of the knee joint of the user in walking. If there is the clearance angle in the flexion direction of the knee joint of the user, the flexion of the knee of the user may not be excessively restricted. Accordingly, when the user swings the leg backward immediately after pushing off the leg (e.g., when the hip joint of the user is extended), the knee joint linked to the hip joint may be extended together and may prevent, for example, a foot from hitting the ground.

If the distance d between the hole 186 and the slider 182 reaches the minimum distance, the buffering member 184 may decrease an impact occurring due to a collision between the slider 182 and the base 181.

The bush 185 may be disposed between the slider 182 and the base 181, and may decrease a friction between slider 182 and the base 181 and may assist the slider 182 to smoothly slide.

Figure 5:
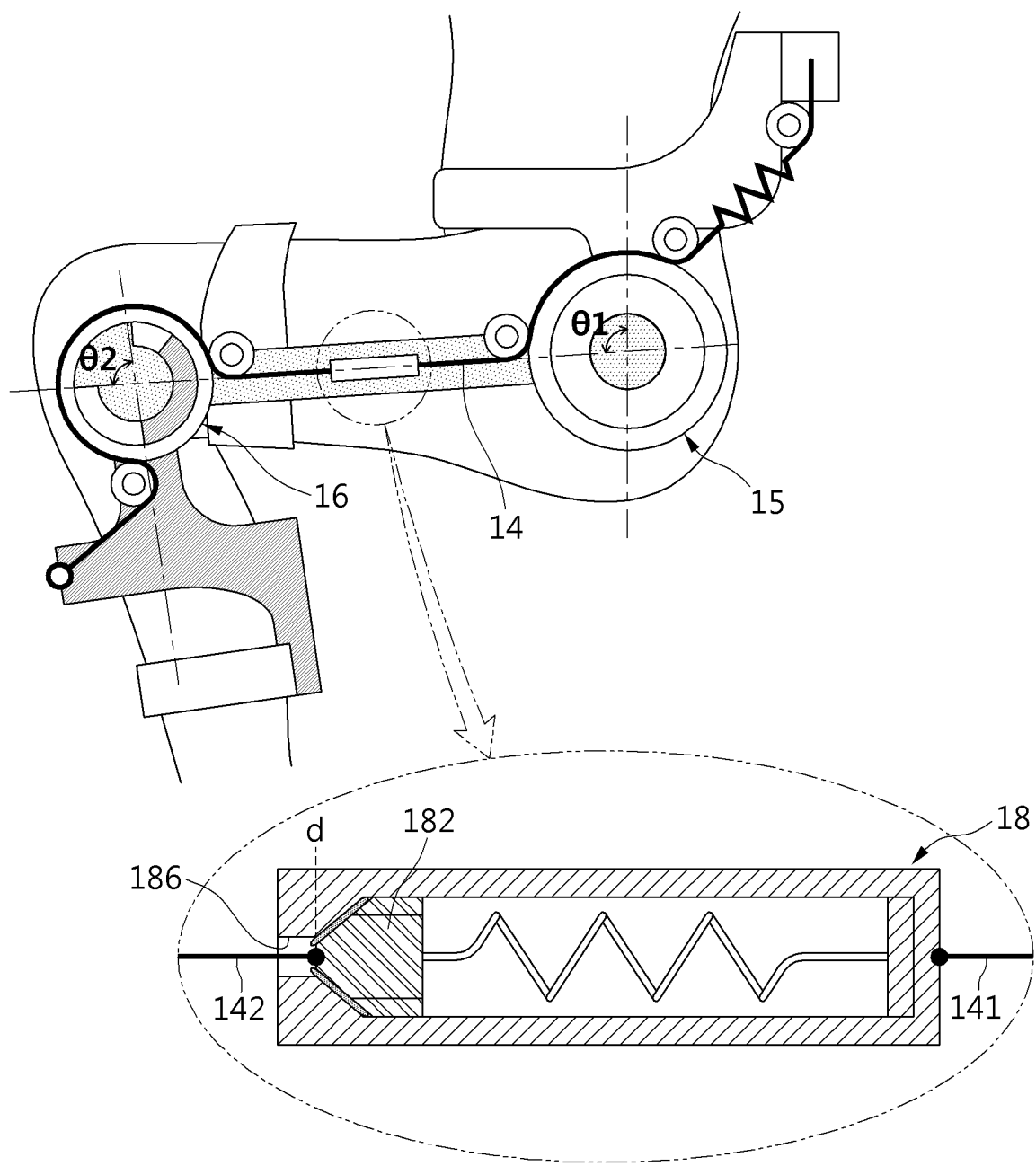
FIG. 5 illustrates an example of a slack adjusting device when a leg of a user wearing a motion assistance apparatus according to at least one example embodiment is in a flexion state.
Figure 6:
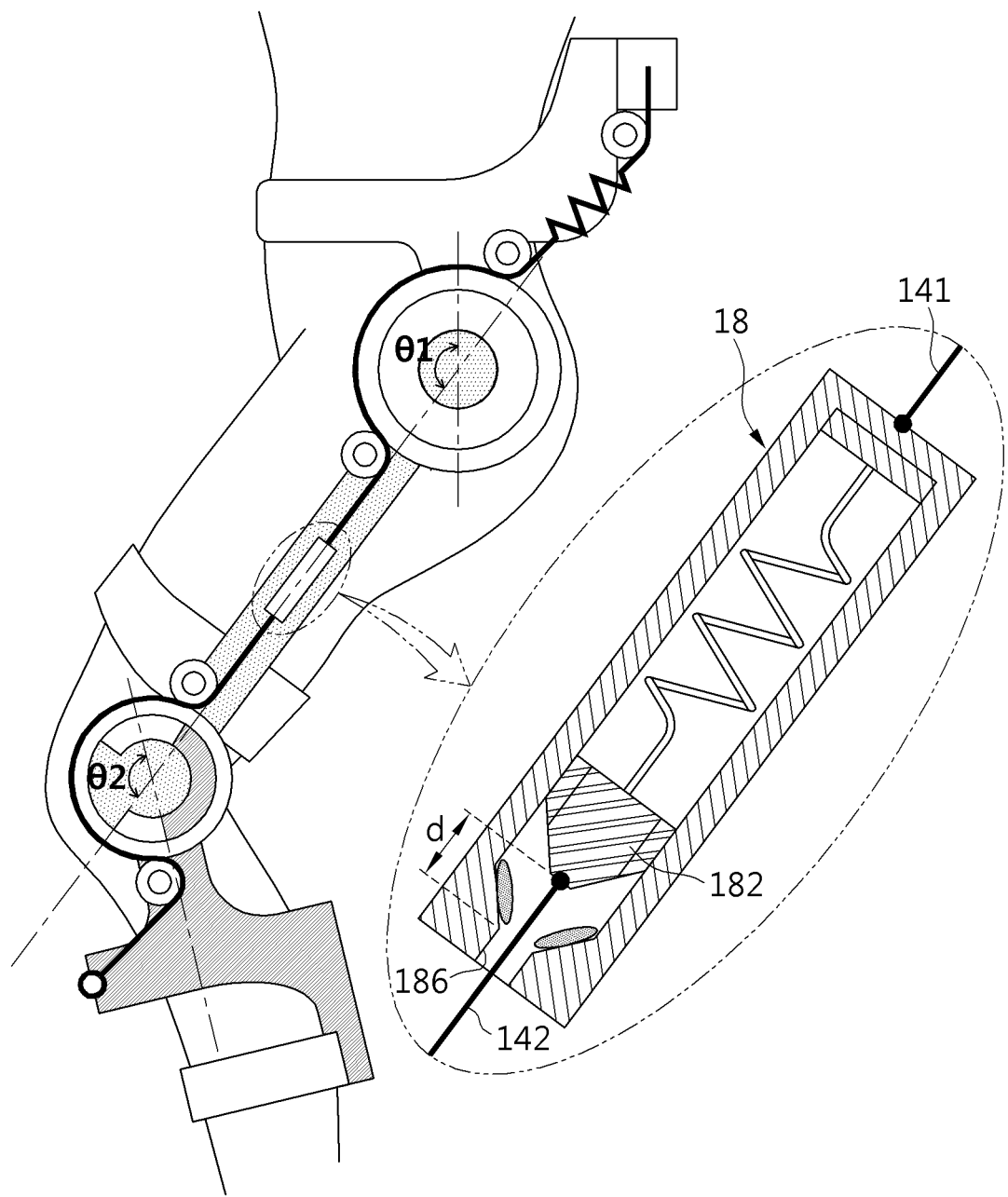
FIG. 6 illustrates an example of an operation of a slack adjusting device while the leg of the user of FIG. 5 is being extended.
Figure 7:
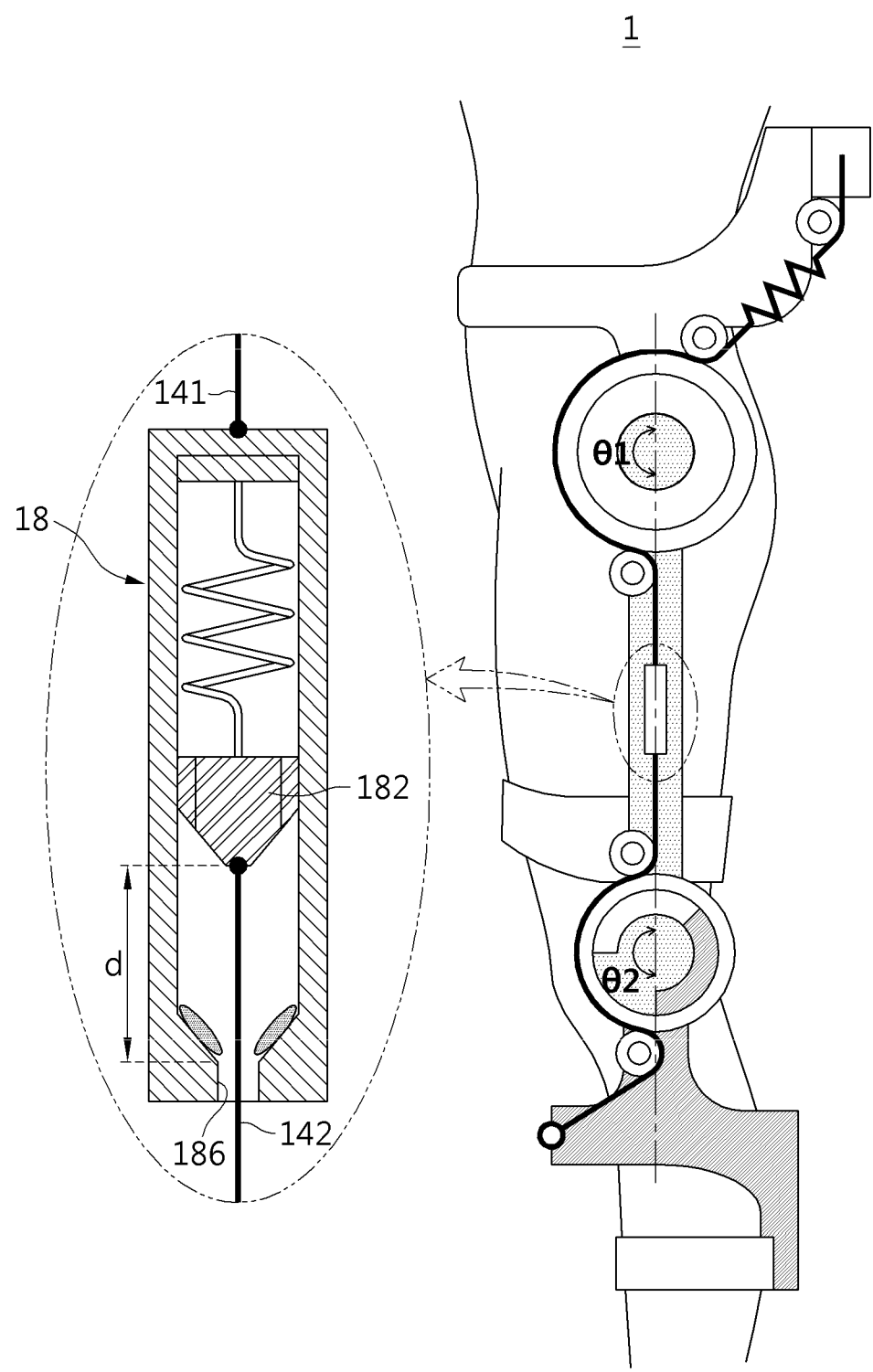
FIG. 7 illustrates an example of a slack adjusting device when a leg of a user wearing a motion assistance apparatus according to at least one example embodiment is in an extension state.

FIG. 5 illustrates an example of a slack adjusting device when a leg of a user wearing a motion assistance apparatus according to at least one example embodiment is in a flexion state, FIG. 6 illustrates an example of an operation of a slack adjusting device while the leg of the user of FIG. 5 is being extended. FIG. 7 illustrates an example of a slack adjusting device when a leg of a user wearing a motion assistance apparatus according to at least one example embodiment is in an extension state.

Referring to FIGS. 5 through 7, the motion assistance apparatus 1 may assist only a hip joint of a user based on a motion state of the user, or may simultaneously assist (or assist both) the hip joint and a knee joint of the user. For example, referring to FIG. 5, when the user is squatting or ascending stairs, the distance d between the hole 186 and the slider 182 in the slack adjusting device 18 may reach the minimum distance. In this case, a length of the first cable 141 that is wound around the first joint 15 may increase or decrease, and a length of the second cable 142 that is wound around the second joint 16 may decrease or increase by the increased or decreased length. In this manner, the first angle θ1 and the second angle θ2 may interact. As another example, referring to FIGS. 6 and 7, when the user is walking or standing, the distance d between the hole 186 and the slider 182 in the slack adjusting device 18 may be greater than the minimum distance and an allowable distance of the slider 182 to be movable in the base 181 may be secured. In this case, if an increase in the length of the second cable 142 that is wound around the second joint 16 is within the allowable distance, the length of the first cable 141 that is wound around the first joint 15 may not vary. Accordingly, the first angle θ1 and the second angle θ2 may not interact. Although the hip joint is fixed, the user may bend or extend the knee.

Figure 8:
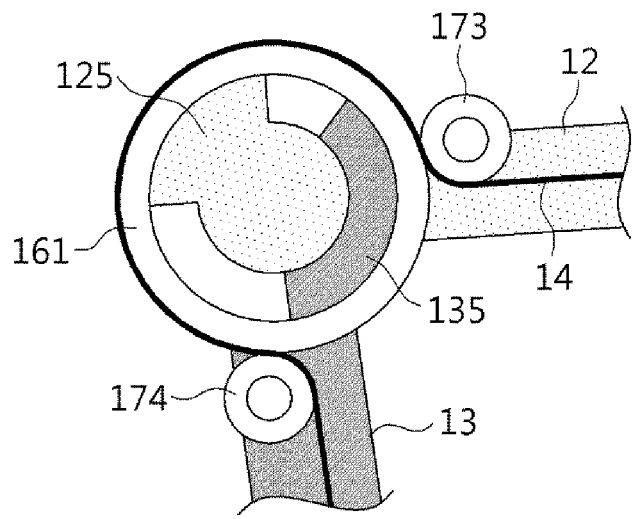
FIG. 8 illustrates an example in which an engager is stopped at a second frame according to at least one example embodiment.
Figure 8:
Figure 8:
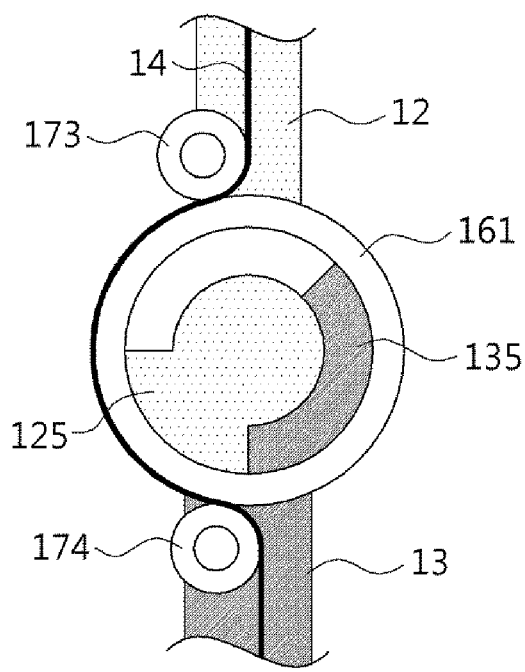

FIG. 8 illustrates an example in which an engager is stopped at a second frame according to at least one example embodiment.

Referring to FIG. 8, the connection frame 12 may include an engager 125 configured to restrict the second angle θ2 between the connection frame 12 and the second frame 13 to be less than or equal to a desired (or alternatively, predetermined) angle. For example, the engager 125 may be in a shape protruded from one side of the connection frame 12. For example, the second frame 13 may include a hinge connector 135 that is hinge-connected to the connection frame 12. The engager 125 may be engaged with the hinge connector 135 in response to relative rotation of the connection frame 12 and the second frame 13. The engager 125 may prevent a hyper extension of the knee of the user.

Figure 9:
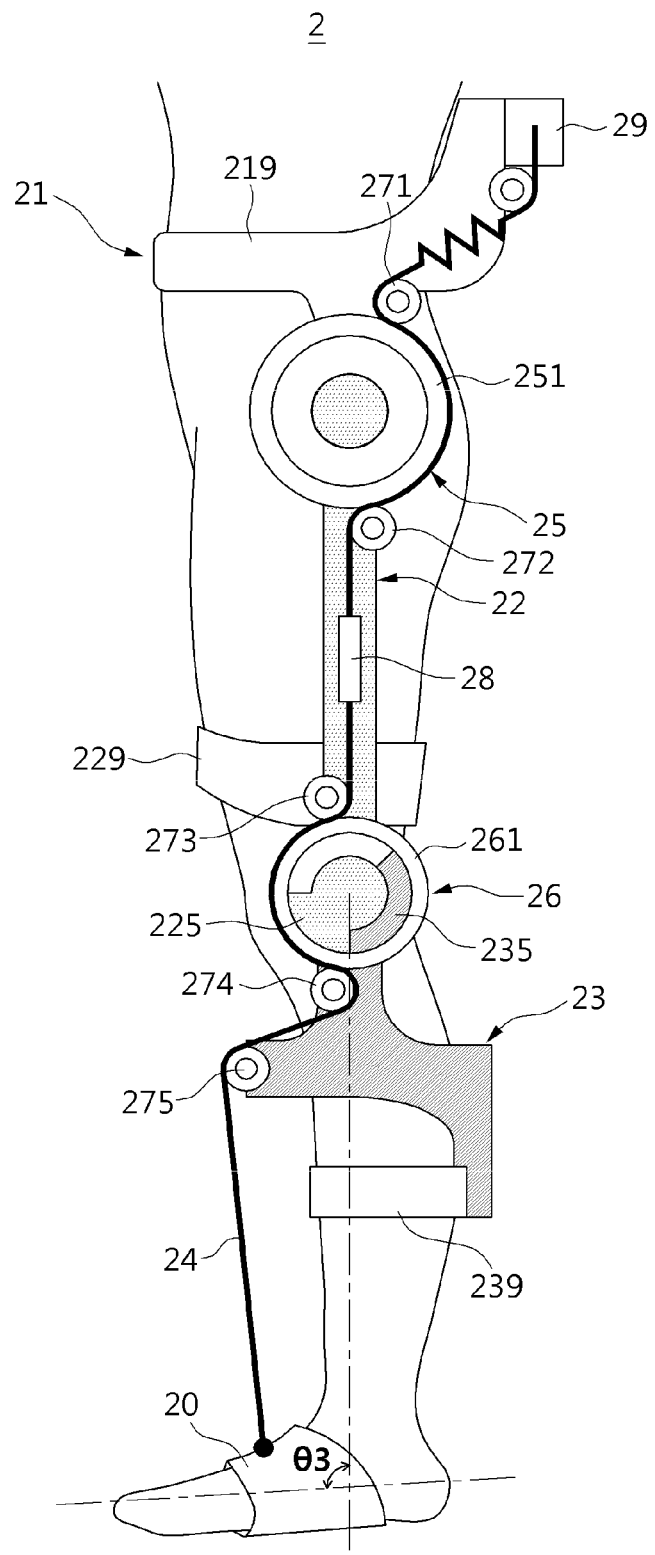
FIG. 9 is a side view of a motion assistance apparatus according to at least one example embodiment.
Figure 10:
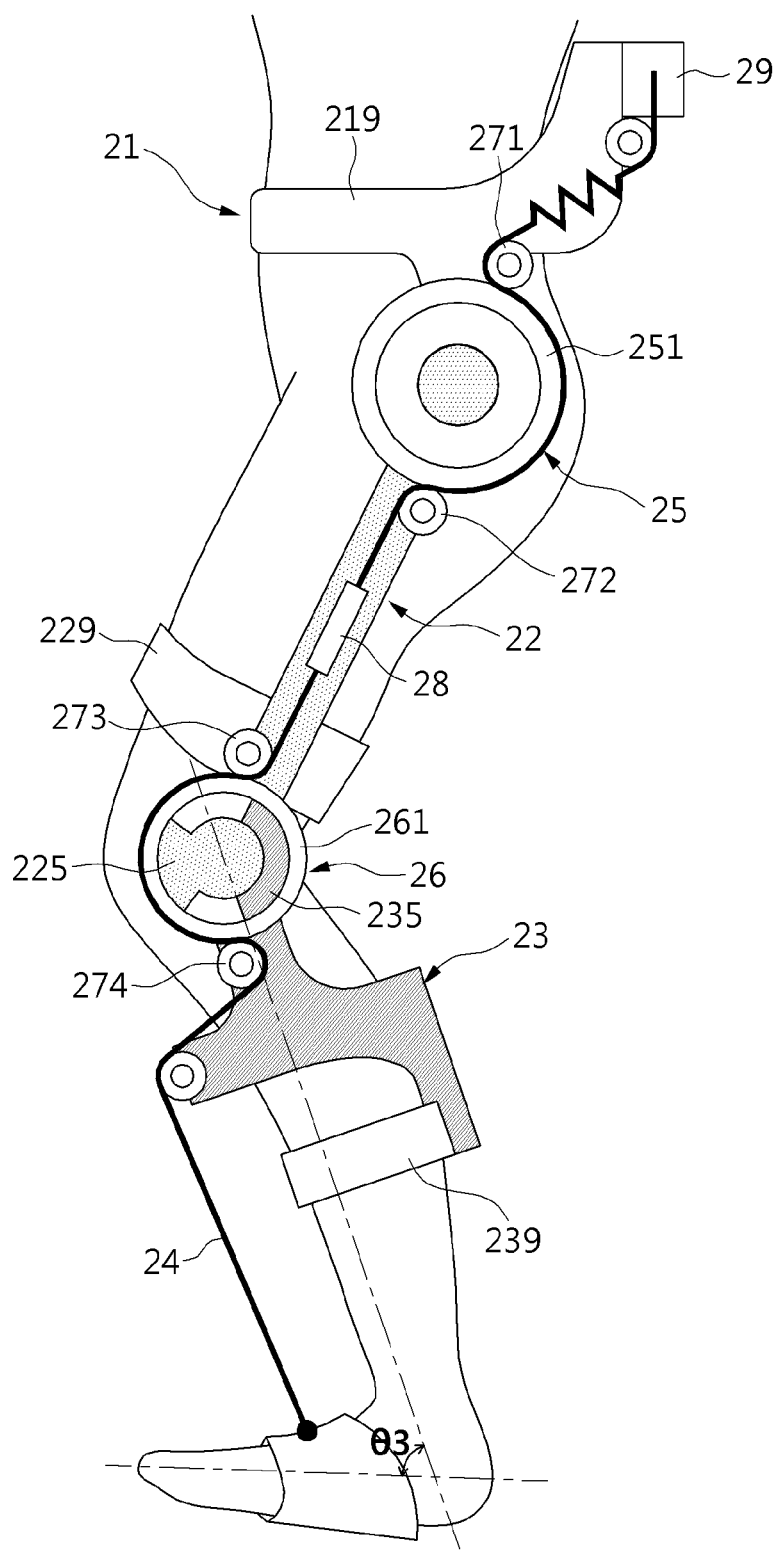
FIG. 10 is a side view of a motion assistance apparatus according to at least one example embodiment.

FIGS. 9 and 10 are side views of a motion assistance apparatus according to at least one example embodiment.

Referring to FIGS. 9 and 10, a motion assistance apparatus 2 may include a first frame 21, a connection frame 22, a second frame 23, a third frame 20, a power transmission member 24, a first joint 25, a second joint 26, guides 271, 272, 273, 274, and 275, a slack adjusting device 28, and a length adjusting device 29.

The third frame 20 may support a fourth part of the user that is connected to a third part of the user through a single joint. For example, the third frame 20 may support a foot that is connected to a thigh through an ankle joint, that is, a talocrural joint. The third frame 20 may include a third support configured to surround the fourth part of the user. The third support may include a detachable belt that enables the user to conveniently wear the motion assistance apparatus 2.

The power transmission member 24 may change a third angle θ3 between the second frame 23 and the third frame 20 based on a length of the power transmission member 24 that is wound around the first joint 25 and the second joint 26. For example, in response to the hip joint of the user and the knee joint of the user moving in a flexion direction, the power transmission member 24 may be wound around the first joint 25 and the second joint 26. In this case, to secure the length of the power transmission member 24 that is wound around the first joint 25 and the second joint 26, the power transmission member 24 may pull the third frame 20 and the third angle θ3 may decrease.

According to the above structure, the motion assistance apparatus 2 may assist a flexion of the hip joint and the ankle of the user in a right-after-push-off stage in which the foot is positioned closest to the ground during a walking cycle of the user. The motion assistance apparatus 2 may assist the user with the degraded ankle muscular and nervous functions with the hip joint and the ankle movement. Accordingly, an ankle muscular power assist effect and a fall prevention effect may be achieved.

Some example embodiments of the inventive concepts have been described. It will be obvious that the example embodiments may be varied in many ways. Such variations are not to be regarded as a departure from the intended spirit and scope of example embodiments of the inventive concepts, and all such modifications as would be obvious to one skilled in the art are intended to be included within the scope of the following claims.

What is claimed is:

1. A motion assistance apparatus comprising:
a first frame;
a connection frame connected to the first frame, the connection frame configured to rotate relative to the first frame;
a second frame connected to the connection frame, the second frame configured to rotate relative to the connection frame;
a power transmission member configured to change, based on a first angle between the first frame and the connection frame, a second angle between the connection frame and the second frame;
a first joint configured to connect the first frame and the connection frame;
a second joint configured to connect the connection frame and the second frame;
a first guide on the first frame, the first guide adjacent to the first joint, and the first guide configured to guide the power transmission member to be in contact with a portion of an outer circumference of the first joint;
a second guide on the connection frame, the second guide adjacent to the first joint, and the second guide configured to guide the power transmission member to be in contact with another portion of the outer circumference of the first joint;
a third guide on the connection frame, the third guide adjacent to the second joint, and the third guide configured to guide the power transmission member to be in contact with a portion of an outer circumference of the second joint; and a fourth guide on the second frame, the fourth guide adjacent to the second joint, and the fourth guide configured to guide the power transmission member to be in contact with another portion of the outer circumference of the second joint.

2. The motion assistance apparatus of claim 1, wherein the first joint comprises a first idler configured to rotate on an outer-surface of the first joint, and the second joint comprises a second idler configured to rotate on an outer surface of the second joint, and the power transmission member is configured to wind around the first idler and the second idler.

3. The motion assistance apparatus of claim 1, wherein, in response to the connection frame rotating in a direction in which the first angle increases relative to the first frame, a length of the power transmission member wound around the first joint increases, a length of the power transmission member wound around the second joint decreases, and the second angle increases.

4. The motion assistance apparatus of claim 1, wherein, in response to the connection frame rotating in a direction in which the first angle decreases relative to the first frame, a length of the power transmission member wound around the first joint decreases, a length of the power transmission member wound around the second joint increases, the second angle decreases, and a variation of the length of the power transmission member wound around the second joint is to be less than or equal to a variation of the length of the power transmission member wound around the first joint.

5. The motion assistance apparatus of claim 1, wherein the power transmission member is configured to wind around the first guide, the first joint, the second guide, the third guide, the second joint, and the fourth guide sequentially.

6. The motion assistance apparatus of claim 1, wherein at least one of the first guide, the second guide, the third guide, and the fourth guide is configured to rotate.

7. The motion assistance apparatus of claim 1, wherein both ends of the power transmission member are fixed to the first frame and the second frame, respectively.

8. The motion assistance apparatus of claim 7, wherein at least one of the first frame and the second frame further comprises a length adjusting device configured to adjust a length of the power transmission member, and one end of the power transmission member is fixed to the length adjusting device.

9. The motion assistance apparatus of claim 8, wherein the length adjusting device comprises:

a pinion gear to which one end of the power transmission member is fixed; and a worm gear configured to engage into the pinion gear.

10. The motion assistance apparatus of claim 1, wherein the power transmission member has elasticity.

11. The motion assistance apparatus of claim 1, wherein the power transmission member comprises:

a first cable configured to connect to the first frame;

a second cable configured to connect to the second frame; and a slack adjusting device configured to connect to both the first cable and the second cable.

12. The motion assistance apparatus of claim 11, wherein the slack adjusting device comprises:

a base configured to connect to one of the first cable and the second cable;

a slider configured to connect to another one of the first cable and the second cable, the slider configured to slide along the base; and an elastic body between the slider and the base.

13. The motion assistance apparatus of claim 12, wherein the slack adjusting device further comprises:

a buffering member configured to buffer an impact of the slider against the base.

14. The motion assistance apparatus of claim 1, wherein the connection frame comprises an engager configured to restrict an angle between the connection frame and the second frame to be a threshold angle or less.

15. The motion assistance apparatus of claim 1, wherein the first frame comprises a first support, the first support configured to support a first part of a user, the connection frame comprises a connection support, the connection support configured to support a second part of the user, the second part connected to the first part through a single joint, and the second frame comprises a second support, the second support configured to support a third part of the user, the third part connected to the second part through a single joint.

* * * * *